United States Patent [19]
Franks

[11] Patent Number: 4,968,623
[45] Date of Patent: Nov. 6, 1990

[54] CELL CULTURE APPARATUS

[75] Inventor: Joseph Franks, Middlesex, England

[73] Assignee: Ion Tech Limited, Middlesex, England

[21] Appl. No.: 389,588

[22] Filed: Aug. 4, 1989

[30] Foreign Application Priority Data

Aug. 4, 1988 [GB] United Kingdom ............... 8818527
Aug. 15, 1988 [GB] United Kingdom ............... 8819341

[51] Int. Cl.⁵ ................................................ C12M 3/04
[52] U.S. Cl. ...................................... 435/285; 435/301; 435/296
[58] Field of Search ............... 435/284, 283, 285, 300, 435/301, 297, 298, 293, 296; 428/131

[56] References Cited

U.S. PATENT DOCUMENTS 3,976,547  8/1976  NcAleer et al. ............... 435/285
4,839,215  6/1989  Starling et al. ............... 428/131

FOREIGN PATENT DOCUMENTS 1187433  5/1985  Canada ............................. 435/285

OTHER PUBLICATIONS

Takada et al., "Cell Affinity of Pyrolytic Carbon-The Effect Exerted on the Growth and Colony—Forming Ability of Cell Lines: L1219, Sq79 and L181", *J. Nihon Univ. Sch. Dent.*, 27(i), 6/1985, pp. 35-45.

*Primary Examiner*—James C. Yeung
*Attorney, Agent, or Firm*—Lowe, Price, Leblanc, Becker & Shur

[57] ABSTRACT

Cell Culture apparatus provides a surface for cell culture, the surface being formed from the group of diamond-like carbon, pyrolytic carbon, glassy carbon and turbostratic carbon. The surface may be part of the container for the culture medium or the surface of microcarriers, such as beads of glass or polymers.

3 Claims, 2 Drawing Sheets

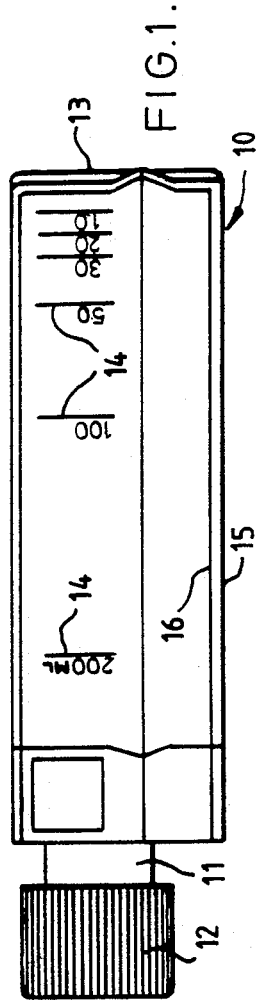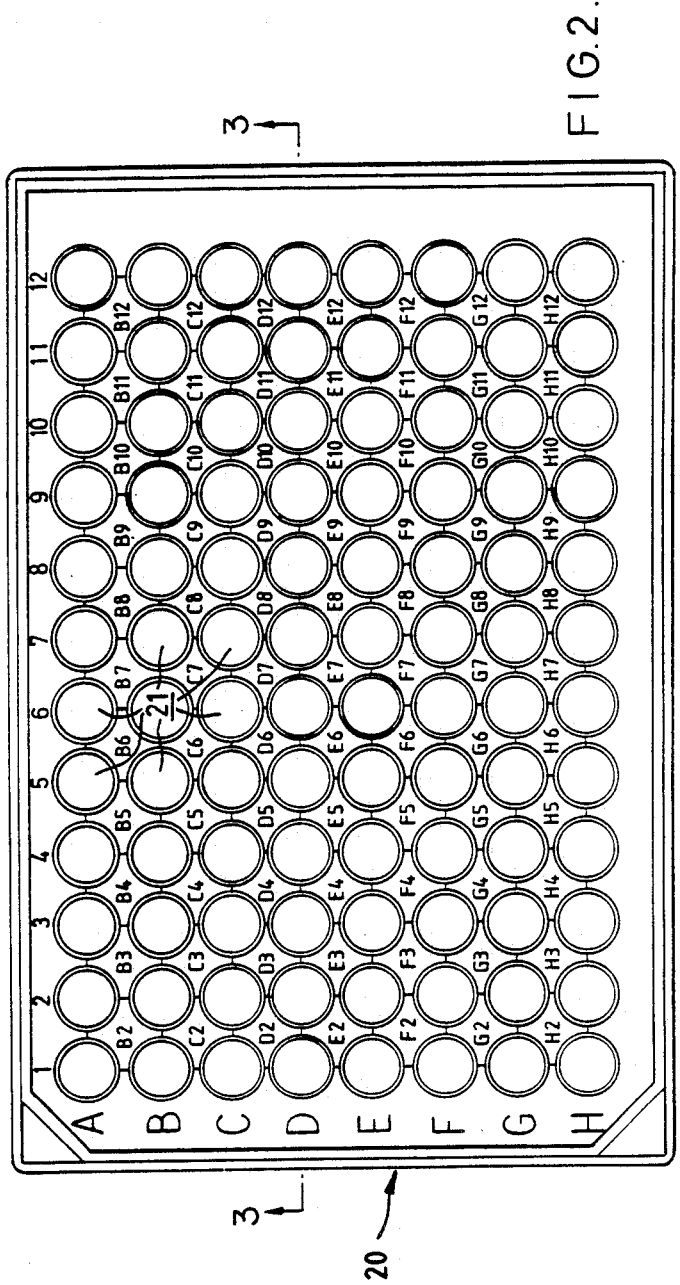

CELL CULTURE APPARATUS

Cell culture apparatus comprises a plurality of containers the shape, size and content of which is chosen to suit a particular aspect of culture preparation. Glass and plastics have been used to form the containers.

In order to nourish the cells during growth, special growth media is included with the cells in the container. A large range of cell types known as 'Anchorage Dependent' cells require a surface upon which to grow either directly or with an intermediate layer of other protinaceous material. This we call a culture surface. In order to promote the improved growth of cells in cell culture apparatus it has been suggested to treat the culture surface of the containers by spark erosion or to impregnate the culture surface with protinaceous material such as collagen, but such treatment is expensive.

According to the present invention, there is provided cell culture apparatus in which the culture surface of the containers comprises a form of carbon selected from the group of diamond-like carbon, pyrolytic carbon, glassy carbon and turbostratic carbon. We have found that such materials attract proteins and so provide a uniform distribution of cell growing sites. It would be possible for the containers to be formed from one or more of these carbon materials, or the containers could comprise a substrate of another material coated with a said form of carbon.

Examples of the invention will now be described with reference to the accompanying drawings in which:

FIG. 1 is a side elevation of a tissue culture flask.

FIG. 2 shows a plan of and a vertical section through a multi-well plate.

Figure 3:
FIG. 3 is a relevant section on line A—A of FIG. 2

Cells usually in solution, are inserted into a tissue culture flask illustrated in FIG. 1 through an inlet 11 closed by a stopper 12, the flask being arranged with wall 13 as its box. Growth Medium or nutrient solution is also inserted into the flask through the inlet 11 in a desired quantity up to a level marked by lines 14 on the wall of the flask which is of transparent material.

The flask is then sealed by the stopper 12 and arranged with the wall 15 as its base in a room or container maintained at a temperature convenient for the incubation of the cells. It is sometimes desirable occasionally to rock the flask to provoke movement of the growth medium across the cells. The interior face 16 of the wall 15 is a culture surface. At periods throughout the growth of the cells, the cells are examined through a microscope.

In another example, cells, usually in solution, are inserted into one or more wells 21 in a multi-well plate 20 shown in FIGS. 2 and 3. Growth medium is placed on top and the well plates covered with a lid (not shown) and placed in an incubator. As can be seen in FIG. 3, the wells 21 are rectangular in vertical section and have their upper edges 22 in a horizontal plane. The well plate has an outer rim 24 slightly above this plane which rim locates the lid. After incubation the grown cells are examined under a microscope. It is desirable therefore, that at least the base of the wells be transparent.

In another example, microcarriers 30 typically small beads of glass, polymeric or other materials about 2 mm in diameter. They are contained in large numbers shown only diagrammatically in a vessel 31 shown in FIG. 4 and their surface used as a culture surface. This enables both a large culture surface to be contained in a small volume and, particularly with stirring, good contact between the growth medium and the cells growing on the culture surface. The vessel 31 is a vertical cylinder encircled by a heating jacket 32. A peristaltic pump 33 forces microcarrier culture from a heated reservoir 36 through the cylinder from bottom to top and back to the reservoir. Filters 34 are provided at the top and bottom of the reservoir. Gas is supplied by a conduit 35 to the reservoir above the medium surface.

Figure 4:
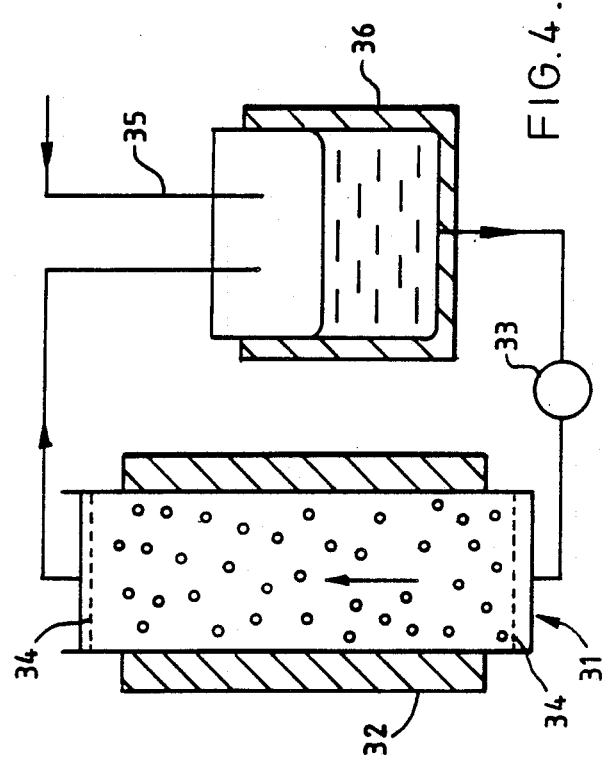
FIG. 4 is a diagrammatic representation of a microcarrier culture system.

Microcarriers can be added to the growth medium in Tissue Culture Flasks (see FIG. 1) or multi-well trays (see FIG. 2) to enhance cell growth or can be used in a dedicated vessel through which the growth medium is passed as in FIG. 4. In this latter fashion Microcarriers can be used as an active surface inside a chromatographic column.

The apparatus of these examples, each with their cell supporting surface of said form of carbon, is used in the conventional way. Anchorage-dependent cells to be grown are placed in the container together with growth medium. The cells adhere directly to the surface or to proteins from the growth medium already adhering to the surface. Since this adherence is enhanced when the surface is coated with said form of carbon the efficiency of growth is improved.

What is claimed is:

1. Cell culture apparatus including containers having a culture surface, wherein the culture surface of the containers comprises a form of carbon selected from the group of diamond-like carbon and turbostratic carbon.

2. Apparatus as claimed in claim 1 wherein the culture surface comprises a plurality of said forms of carbon.

3. Apparatus as claimed in claim 1 wherein the culture surface comprises said form of carbon coated into a substrate.

* * * * *